(12) United States Patent
Spitler

(10) Patent No.: US 9,763,706 B2
(45) Date of Patent: Sep. 19, 2017

(54) INTERSPINOUS FUSION DEVICE

(71) Applicant: James Spitler, Boca Raton, FL (US)

(72) Inventor: James Spitler, Boca Raton, FL (US)

(73) Assignee: FloSpine, LLC, Boca Raton, FL (US)

(*) Notice: Subject to any disclaimer, the term of this patent is extended or adjusted under 35 U.S.C. 154(b) by 0 days.

(21) Appl. No.: 14/826,242

(22) Filed: Aug. 14, 2015

(65) Prior Publication Data

US 2016/0045231 A1 Feb. 18, 2016

Related U.S. Application Data

(60) Provisional application No. 62/037,131, filed on Aug. 14, 2014.

(51) Int. Cl.
*A61B 17/70* (2006.01)
*A61B 17/68* (2006.01)

(52) U.S. Cl.
CPC ...... *A61B 17/7067* (2013.01); *A61B 17/7068* (2013.01); *A61B 2017/681* (2013.01)

(58) Field of Classification Search
CPC ............ A61B 17/7044; A61B 17/7047; A61B 17/7062; A61B 17/7065; A61B 17/7067; A61B 17/7068; A61B 17/707; A61B 17/7071; A61B 17/8038; A61B 17/8042
See application file for complete search history.

(56) References Cited

U.S. PATENT DOCUMENTS

| | | | | |
|---|---|---|---|---|
| 7,063,701 B2* | 6/2006 | Michelson | ......... | A61B 17/8605 606/307 |
| 7,691,133 B2* | 4/2010 | Partin | ................. | A61B 17/683 606/289 |
| 7,727,233 B2* | 6/2010 | Blackwell | .......... | A61B 17/7068 606/251 |
| 7,806,911 B2* | 10/2010 | Peckham | ........... | A61B 17/7059 606/248 |
| 8,128,659 B2* | 3/2012 | Ginsberg | ........... | A61B 17/7068 606/246 |
| 8,206,420 B2* | 6/2012 | Patel | .................. | A61B 17/7065 606/247 |
| 8,236,031 B2* | 8/2012 | Bucci | ................. | A61B 17/7062 606/248 |
| 8,343,190 B1* | 1/2013 | Mueller | ............. | A61B 17/7068 606/248 |
| 8,419,738 B2* | 4/2013 | Smisson, III | ...... | A61B 17/7067 606/86 A |

(Continued)

*Primary Examiner* — Lynnsy Summitt
(74) *Attorney, Agent, or Firm* — Clements Bernard Walker PLLC; Christopher L. Bernard

(57) ABSTRACT

An interspinous fusion device for holding adjacent spinous processes of a spine of a patient in a fixed configuration, including: a first plate configured to engage one side of the adjacent spinous processes; a second plate configured to engage another side of the adjacent spinous processes opposite the one side of the adjacent spinous processes; and a spacer disposed between and coupling the first plate to the second plate, wherein the spacer allows one or more of the first plate and the second plate to pivot relative to the other plate in a first unlocked configuration and prevents one or more of the first plate and the second plate from pivoting relative to the other plate in a second locked configuration. Each of the first plate and the second plate includes a pair of opposed wing members protruding from a central bore.

21 Claims, 5 Drawing Sheets

(56) References Cited

U.S. PATENT DOCUMENTS

| | | | | |
|---|---|---|---|---|
| 8,425,560 B2* | 4/2013 | Massoudi | A61B 17/7068 | 606/249 |
| 8,439,953 B2* | 5/2013 | Mitchell | A61B 17/1606 | 606/246 |
| 8,568,453 B2* | 10/2013 | Abdou | A61B 17/7068 | 606/248 |
| 8,603,143 B2* | 12/2013 | Robinson | A61B 17/7068 | 606/249 |
| 8,636,772 B2* | 1/2014 | Schmierer | A61B 17/1671 | 606/248 |
| 8,652,183 B1* | 2/2014 | Truman | A61B 17/8038 | 606/281 |
| 8,721,686 B2* | 5/2014 | Gordon | A61B 17/7068 | 606/248 |
| 8,821,547 B2* | 9/2014 | Dryer | A61B 17/7062 | 606/248 |
| 8,882,805 B1* | 11/2014 | Maccree | A61B 17/7067 | 606/249 |
| 9,072,550 B2* | 7/2015 | Lange | A61B 17/7067 | |
| 9,168,073 B2* | 10/2015 | Aschmann | A61B 17/7068 | |
| 9,192,414 B2* | 11/2015 | Haas | A61B 17/7062 | |
| 9,198,697 B2* | 12/2015 | Zappacosta | A61B 17/7065 | |
| 9,198,769 B2* | 12/2015 | Perrow | A61B 17/8042 | |
| 9,211,147 B2* | 12/2015 | Gordon | A61B 17/7068 | |
| 9,247,968 B2* | 2/2016 | Taber | A61B 17/7068 | |
| 9,265,532 B2* | 2/2016 | Lamborne | A61B 17/7068 | |
| 2008/0114455 A1* | 5/2008 | Lange | A61B 17/7062 | 623/17.16 |
| 2008/0183218 A1* | 7/2008 | Mueller | A61B 17/7068 | 606/280 |
| 2010/0036419 A1* | 2/2010 | Patel | A61B 17/7065 | 606/249 |
| 2010/0331887 A1* | 12/2010 | Jackson | A61B 17/7008 | 606/264 |
| 2011/0022090 A1* | 1/2011 | Gordon | A61B 17/7068 | 606/249 |
| 2011/0066186 A1* | 3/2011 | Boyer, II | A61B 17/7065 | 606/249 |
| 2011/0184468 A1* | 7/2011 | Metcalf, Jr. | A61B 17/7068 | 606/279 |
| 2012/0101528 A1* | 4/2012 | Souza | A61B 17/7068 | 606/249 |
| 2012/0109203 A1* | 5/2012 | Dryer | A61B 17/7068 | 606/249 |
| 2012/0150228 A1* | 6/2012 | Zappacosta | A61B 17/7068 | 606/248 |
| 2013/0090689 A1* | 4/2013 | Villavicencio | A61B 17/8685 | 606/249 |
| 2013/0103086 A1* | 4/2013 | Marik | A61B 17/7068 | 606/246 |
| 2013/0184752 A1* | 7/2013 | Binder | A61B 17/7068 | 606/248 |
| 2013/0190820 A1* | 7/2013 | Siegfried | A61B 17/7068 | 606/248 |
| 2013/0197581 A1* | 8/2013 | Justis | A61B 17/7068 | 606/248 |
| 2013/0253585 A1* | 9/2013 | Garcia | A61B 17/7067 | 606/249 |
| 2013/0345755 A1* | 12/2013 | Prajapati | A61B 17/7007 | 606/273 |
| 2014/0081331 A1* | 3/2014 | Zappacosta | A61B 17/7068 | 606/249 |
| 2014/0114355 A1* | 4/2014 | Robinson | A61B 17/7068 | 606/249 |
| 2014/0243897 A1* | 8/2014 | Massoudi | A61B 17/7067 | 606/249 |
| 2014/0277138 A1* | 9/2014 | Lange | A61B 17/7059 | 606/246 |
| 2014/0296925 A1* | 10/2014 | Lawson | A61B 17/8033 | 606/289 |
| 2015/0012040 A1* | 1/2015 | Agarwal | A61B 17/7068 | 606/248 |
| 2015/0251014 A1* | 9/2015 | Hirschl | A61N 2/002 | 623/17.16 |
| 2016/0242824 A1* | 8/2016 | Kirschman | A61B 17/7068 | |
| 2016/0249961 A1* | 9/2016 | Okamoto | A61B 17/7068 | |
| 2016/0249962 A1* | 9/2016 | Black | A61B 17/8038 | |

* cited by examiner

INTERSPINOUS FUSION DEVICE

CROSS-REFERENCE TO RELATED APPLICATION

The present patent application/patent claims the benefit of priority of U.S. Provisional Patent Application No. 62/037,131, filed on Aug. 14, 2014, and entitled "INTERSPINOUS PROCESS FUSION SYSTEM," the contents of which are incorporated in full by reference herein.

FIELD OF THE INVENTION

The present invention relates generally to the medical and surgical fields, and especially the spinal surgical field. More specifically, the present invention relates to a novel interspinous fusion device that is configured to (optionally) distract and hold adjacent spinous processes of the spine of a patient in a fixed relationship to one another in the treatment of such conditions as lumbar spinal stenosis and degenerative disc disease, by way of non-limiting example only. Advantageously, the interspinous fusion device of the present invention may be inserted using a conventional open procedure, typically requiring a relatively large incision and a general anesthetic, or using a minimally invasive procedure, typically requiring a relatively small incision and a local anesthetic.

BACKGROUND OF THE INVENTION

Lumbar spinal stenosis, for example, is characterized by a tightening of or decrease in the cross-sectional diameter of the spinal canal and neural foramen, through which the spinal cord and nerve roots of the lumbar (i.e. lower) spine pass, caused by the degeneration of the lumbar discs (through fluid loss and collapse) and the facet joints of the spinal column. In lumbar spinal stenosis, the lumbar discs deteriorate and the lumbar disc spaces collapse, resulting in a portion of the lumbar discs protruding into the ventral or anterior (i.e. front) portion of the spinal canal. At the same time, the two facet joints associated with each lumbar vertebrae become arthritic, growing in size, and protruding into the dorsal or posterior (i.e. back) portion of the spinal canal. Thus, the cross-sectional diameter of the spinal canal is decreased, impinging on the spinal cord and nerve roots of the lumbar spine. In addition, the ligamentum flavum that connect the bases of the spinous processes of the spinal column and the lamina tend to buckle with lumbar disc collapse, further decreasing the cross-sectional diameter of the spinal canal. The neural foramen, through which the nerve roots exit, are pinched with disc collapse and facet joint arthropathy. This condition is especially common in the elderly and symptoms may include remitting or unremitting pain and/or weakness/numbness in the middle to lower back and/or legs when moving and/or stationary. It should be noted that similar problems can occur in the cervical (i.e. upper) spine as well.

Conventional treatments for lumbar spinal stenosis include oral and/or injectable analgesics and/or anti-inflammatory medications (non-steroidal and/or steroidal), activity avoidance and/or physical therapy, braces, and/or surgical procedures. Surgical procedures for lumbar spinal stenosis include laminectomies/laminotomies and/or spinal fusions. In a laminectomy/laminotomy, all or a portion of a given facet joint, lamina, and ligamentum flavum are removed to alleviate compression of the spinal canal. This procedure basically "unroofs" or enlarges a portion of the spinal canal. Additionally, a spinal fusion may be performed. In a spinal fusion, a connecting bar and a bone graft are used to join or fuse adjacent vertebrae via a plurality of pedicle screws, for example, thus stabilizing the vertebral segment. Much, if not all, of a given lumbar disc is removed in conjunction with a spinal fusion. In general, a spinal fusion is most suitable when there is instability or translation between adjacent vertebrae (i.e. spondylolisthesis). Disadvantageously, the plurality of pedicle screws used to perform a spinal fusion may become loose with the passage of time if a non-union develops. Both laminectomies/laminotomies and spinal fusions are major, open procedures, typically utilizing cumbersome equipment and requiring a relatively large incision and a general anesthetic. This may be dangerous for the elderly or the sick. In addition, both procedures are very expensive.

What has been observed clinically is that many patients, when they flex forward, experience an increase in the cross-sectional diameter of the spinal canal and neural foramen, thus alleviating or eliminating their pain and/or weakness/numbness caused by lumbar spinal stenosis. This is caused by the temporary distraction of the spinous processes and the "stretching out" of the ligamentum flavum that connect the bases of the spinous processes and lamina. The collapsed neural foramen are also increased in height and cross-sectional area by the distraction. In other words, the lumbar discs and other structures of the spinal column are temporarily decompressed. This observation has led to improved treatments for lumbar spinal stenosis.

For example, the spinous process distractor for lumbar spinal stenosis disclosed and described by Lee et al. (J. Spinal Disord. Tech., Vol. 17, No. 1, February 2004) provides a main body assembly including a spacer and a universal wing assembly. The main body assembly is disposed between adjacent spinous processes, distracting them, and the universal wing assembly is used to lock the main body assembly in place. Disadvantageously, this spinous process distractor utilizes wings that are relatively fixed in their orientation utilizes, preventing it from effectively accommodating some anatomies, and a nut that must be engaged and tightened, which is prone to "backing out." Other conventional spinous process distractors known to those of ordinary skill in the art suffer from similar shortcomings. None are flexible or elegant enough in their configuration or operation.

Thus, what is still needed in the art is an improved interspinous fusion device that is configured to (optionally) distract and hold adjacent spinous processes of the spine of a patient in a fixed relationship to one another in the treatment of such conditions as lumbar spinal stenosis and degenerative disc disease, by way of non-limiting example only.

BRIEF SUMMARY OF THE INVENTION

In various exemplary embodiments, the present invention provides a novel interspinous fusion device that is configured to (optionally) distract and hold adjacent spinous processes of the spine of a patient in a fixed relationship to one another in the treatment of such conditions as lumbar spinal stenosis and degenerative disc disease, by way of non-limiting example only. Advantageously, the interspinous fusion device of the present invention may be inserted using a conventional open procedure, typically requiring a relatively large incision and a general anesthetic, or using a minimally invasive procedure, typically requiring a relatively small incision and a local anesthetic.

In one exemplary embodiment, the present invention provides an interspinous fusion device for holding adjacent spinous processes of a spine of a patient in a fixed configuration, including: a first plate configured to engage one side of the adjacent spinous processes; a second plate configured to engage another side of the adjacent spinous processes opposite the one side of the adjacent spinous processes; and a spacer disposed between and coupling the first plate to the second plate, wherein the spacer allows one or more of the first plate and the second plate to pivot relative to the other plate in a first unlocked configuration and prevents one or more of the first plate and the second plate from pivoting relative to the other plate in a second locked configuration. Each of the first plate and the second plate includes a pair of opposed wing members protruding from a central bore. Each of the pair of opposed wing members includes a friction surface configured to engage the associated spinous process. The friction surface is pivotably coupled to the associated wing member. The spacer includes a threaded post disposed between and coupling the first plate to the second plate. The threaded post includes a substantially spherical head that is configured to engage a substantially spherical bore of the first plate, thereby allowing the first plate to pivot relative to the second plate in the first unlocked configuration. The threaded post also includes a set screw that is selectively disposed within the substantially spherical head, thereby preventing the first plate from pivoting relative to the second plate in the second locked configuration. The threaded post further includes an externally threaded end that is configured to engage an internally threaded bore of the second plate. The interspinous fusion device also includes a retention member for securing the second plate to the threaded post, such that the threaded post cannot "back out" of the second plate. The spacer further includes a distraction member coupled to the first plate that is selectively disposed between the adjacent spinous processes. The distraction member is one or more of pivotably and rotatably coupled to the first plate.

In another exemplary embodiment, the present invention provides an interspinous fusion method for holding adjacent spinous processes of a spine of a patient in a fixed configuration, including: providing a first plate configured to engage one side of the adjacent spinous processes; providing a second plate configured to engage another side of the adjacent spinous processes opposite the one side of the adjacent spinous processes; and providing a spacer disposed between and coupling the first plate to the second plate, wherein the spacer allows one or more of the first plate and the second plate to pivot relative to the other plate in a first unlocked configuration and prevents one or more of the first plate and the second plate from pivoting relative to the other plate in a second locked configuration. Each of the first plate and the second plate includes a pair of opposed wing members protruding from a central bore. Each of the pair of opposed wing members includes a friction surface configured to engage the associated spinous process. The friction surface is pivotably coupled to the associated wing member. The spacer includes a threaded post disposed between and coupling the first plate to the second plate. The threaded post includes a substantially spherical head that is configured to engage a substantially spherical bore of the first plate, thereby allowing the first plate to pivot relative to the second plate in the first unlocked configuration. The threaded post also includes a set screw that is selectively disposed within the substantially spherical head, thereby preventing the first plate from pivoting relative to the second plate in the second locked configuration. The threaded post further includes an externally threaded end that is configured to engage an internally threaded bore of the second plate. The interspinous fusion method also includes providing a retention member for securing the second plate to the threaded post, such that the threaded post cannot "back out" of the second plate. The spacer further includes a distraction member coupled to the first plate that is selectively disposed between the adjacent spinous processes. The distraction member is one or more of pivotably and rotatably coupled to the first plate.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Again, in various exemplary embodiments, the present invention provides a novel interspinous fusion device that is configured to (optionally) distract and hold adjacent spinous processes of the spine of a patient in a fixed relationship to one another in the treatment of such conditions as lumbar spinal stenosis and degenerative disc disease, by way of non-limiting example only. Advantageously, the interspinous fusion device of the present invention may be inserted using a conventional open procedure, typically requiring a relatively large incision and a general anesthetic, or using a minimally invasive procedure, typically requiring a relatively small incision and a local anesthetic.

Figure 1:
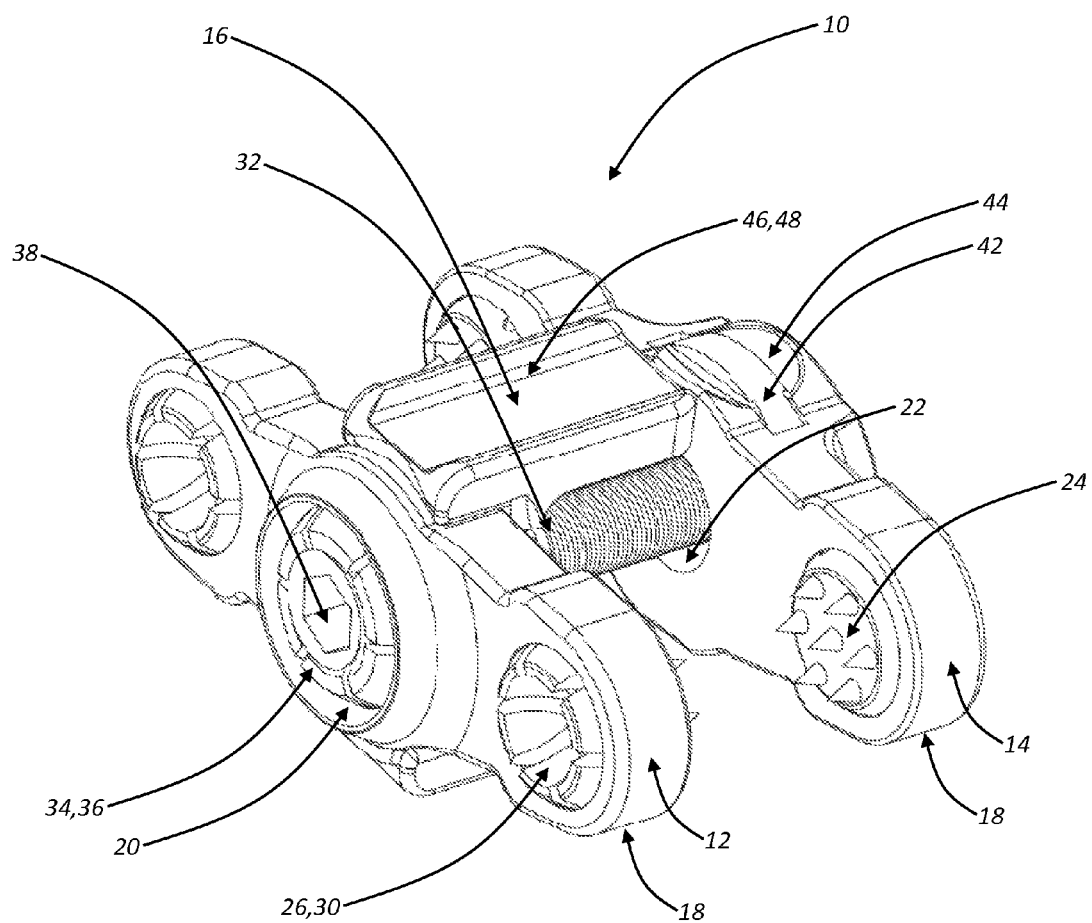
FIG. 1 is a perspective view of one exemplary embodiment of the interspinous fusion device of the present invention, in an assembled configuration.
Figure 2:
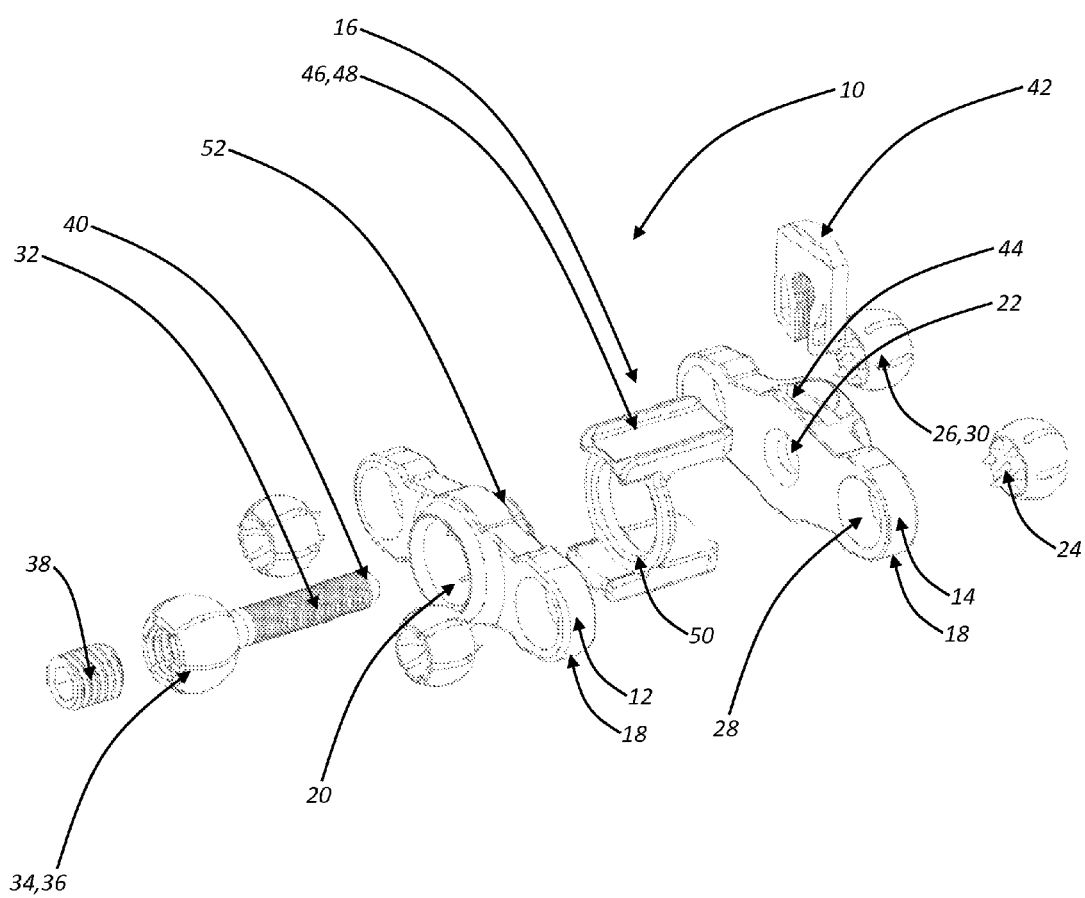
FIG. 2 is an exploded perspective view of one exemplary embodiment of the interspinous fusion device of the present invention, in a disassembled configuration.

Referring now specifically to FIGS. 1 and 2, in one exemplary embodiment, the interspinous fusion device 10 of the present invention may be sized such that it fits a variety of anatomies. The pivoting connection(s) utilized allow the interspinous fusion device 10 to bridge various interspinous gaps of 4-18 mm in 2-mm increments, for example. The interspinous fusion device 10 includes a first plate 12 configured to engage one side of adjacent spinous processes and a second plate 14 configured to engage another side of the adjacent spinous processes opposite the one side of the adjacent spinous processes. In general, a spacer 16 is disposed between the adjacent spinous processes and couples the first plate 12 to the second plate 14. Preferably, the spacer 16 allows one or more of the first plate 12 and the second plate 14 to pivot relative to the other plate (and relative to the adjacent spinous processes) in a first unlocked configuration and prevents one or more of the first plate 12 and the second plate 14 from pivoting relative to the other plate (and relative to the adjacent spinous processes) in a second locked configuration.

Each of the first plate 12 and the second plate 14 includes a pair of opposed wing members 18 protruding from a central bore 20 and 22. Each of the pair of opposed wing members 18 includes a friction surface 24 configured to engage the associated spinous process. In this exemplary embodiment, the friction surface 24 includes a concentrically arranged group or pad of sharpened teeth arranged on the interior, spinous process facing surface of the associated wing member 18. It will be readily apparent to those of ordinary skill in the art, however, that other bone gripping surfaces may also be used. Optionally, the friction surface 24 is pivotably coupled to the associated wing member 18. This is accomplished via spherical bearings 26 that are disposed in spherical voids 28 manufactured into the ends of the wing members 18. These spherical bearings 26 may include appropriate petal structures 30 that allow them to be "snapped" into place and resist "backing out," while allowing them to pivot to some degree within the spherical voids 28. It will be readily apparent to those of ordinary skill in the art that other pivoting configurations may also be utilized.

The spacer 16 includes a threaded post 32 disposed between and coupling the first plate 12 to the second plate 14. Preferably, the threaded post 32 includes a substantially spherical head 34 that is configured to engage the substantially spherical bore 20 of the first plate 12, thereby allowing the first plate 12 to pivot relative to the second plate 14 in the first unlocked configuration. Again, the substantially spherical head 34 may include appropriate petal structures 36 that allow the threaded post 32 to be seated in place, while allowing the threaded post 32 to pivot to some degree within the spherical bore 20. The threaded post 32 also includes a set screw 38 that is selectively disposed within the substantially spherical head 34 and tightened, thereby expanding the petal structures 36 against the spherical bore 20 and preventing the first plate 12 from pivoting relative to the second plate 14 in the second locked configuration. Again, it will be readily apparent to those of ordinary skill in the art that other pivoting configurations may also be utilized.

The threaded post 32 further includes an externally threaded end 40 (FIG. 2) that is configured to engage the internally threaded bore 22 of the second plate 14. In this exemplary embodiment, no pivoting movement is provided between the threaded post 32 and the second plate 14, although such movement may be provided in alternate exemplary embodiments. The interspinous fusion device 10 also includes a retention member 42 for securing the second plate 14 to the threaded post 32, such that the threaded post 32 cannot "back out" of the second plate 14. In this exemplary embodiment, the retention member 42 is an internally threaded clip that is disposed through a port 44 manufactured into the top surface of the second plate 14. This internally threaded clip is disposed about the threaded post 32 within the port 44, the threads of the internally threaded clip catching the threads of the threaded post 32 and capturing the threaded post 32 in position relative to the second plate 14. Preferably, the internally threaded clip is press fit about the threaded post 32, such that it requires a predetermined upward force to remove it. It will be readily apparent to those of ordinary skill in the art that other retainer configurations may also be utilized, from a simple set screw to more complicated mechanisms.

The spacer 16 further includes a distraction member 46 coupled to the first plate 12 (and/or the second plate 14) that is selectively disposed between the adjacent spinous processes. The distraction member 46 is one or more of pivotably and rotatably coupled to the first plate 12 (and/or the second plate 14). In this exemplary embodiment, the distraction member 46 includes one or more planar surfaces 48 that are disposed above and below the threaded post 32 when it is inserted. These planar surfaces 48 are ultimately disposed between the adjacent spinous process and provide a predetermined degree of separation/distraction. The planar surfaces 48 are joined by a ring structure 50 (FIG. 2) that is also disposed about the threaded post 32 when it is inserted. The ring structure engages a corresponding concentric lip structure 52 (FIG. 2) disposed on a back side of the first plate 12 (and/or the second plate 14).

Figure 3:
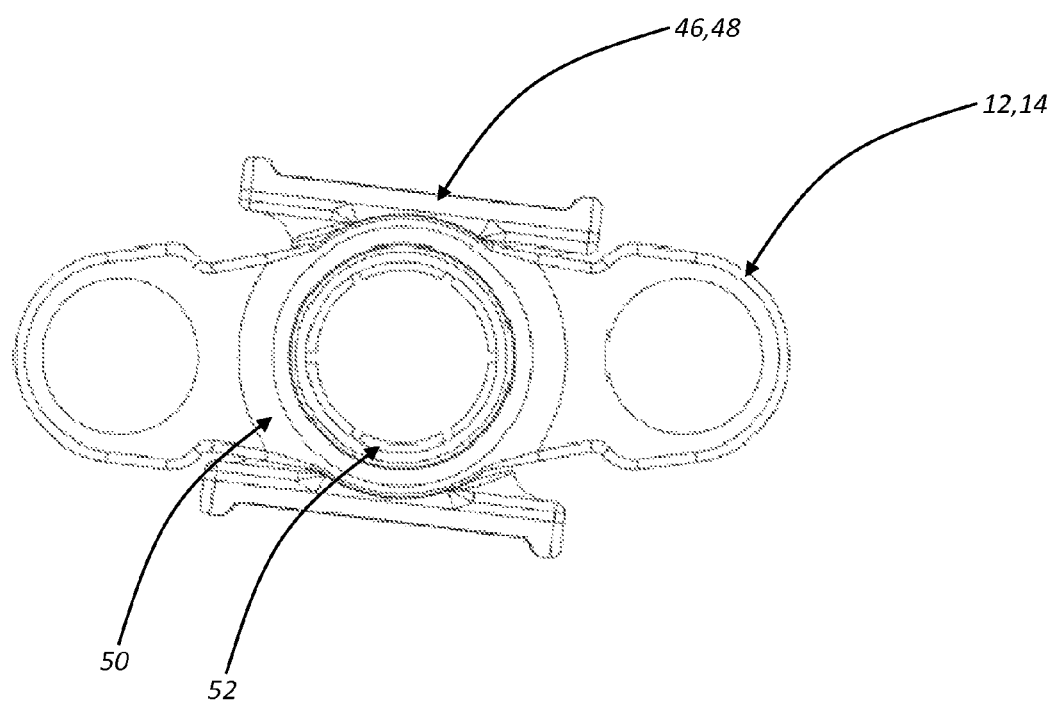
FIG. 3 is a partial planar end view of one exemplary embodiment of the interspinous fusion device of the present invention.

As is illustrated in FIG. 3, this ring/lip interaction allows the spacer 16 to rotate with respect to the first plate 12 and the second plate 14. This rotation is bounded by the interaction of the planar surfaces 48 of the distraction member 46 with the body of the first plate 12 and the second plate 14. Thus, only a finite amount of rotation is allowed.

Figure 4:
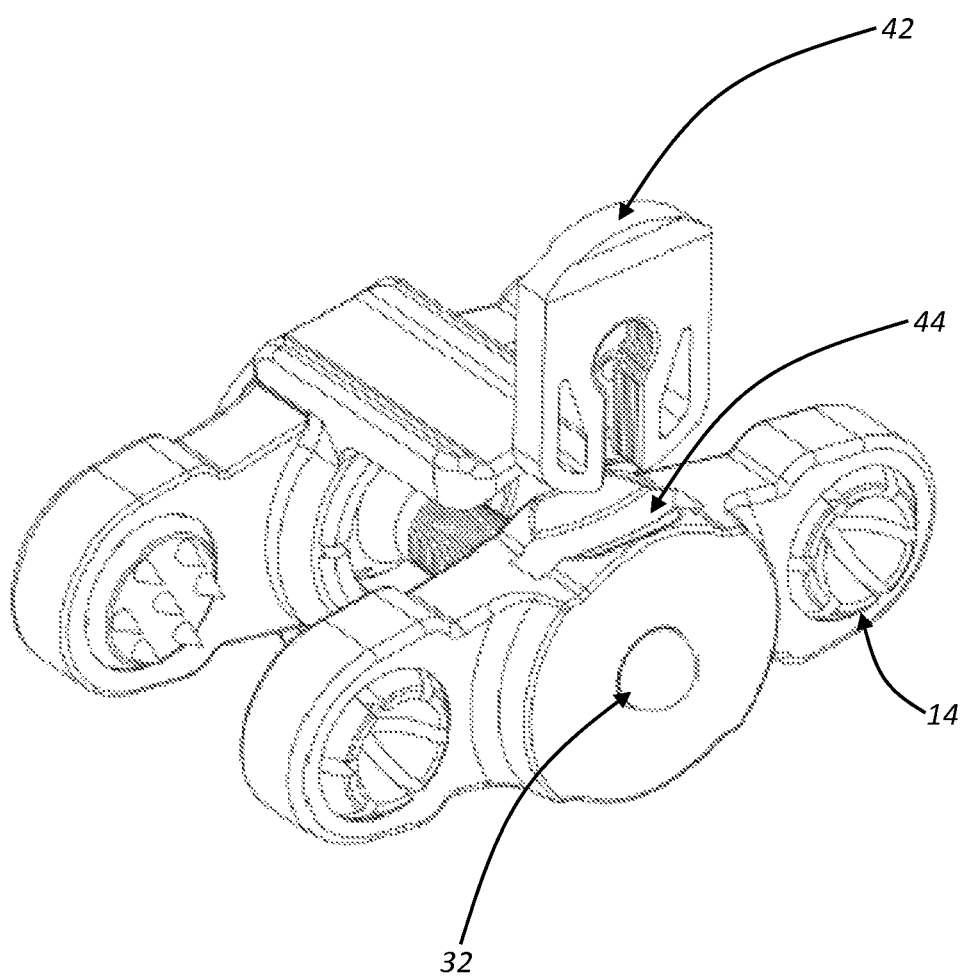
FIG. 4 is a partially exploded perspective view of one exemplary embodiment of the interspinous fusion device of the present invention, in a partially disassembled configuration.

FIG. 4 again illustrates that the retention member 42 is an internally threaded clip that is disposed through a port 44 manufactured into the top surface of the second plate 14. This internally threaded clip is disposed about the threaded post 32 within the port 44, the threads of the internally threaded clip catching the threads of the threaded post 32 and capturing the threaded post 32 in position relative to the second plate 14. Preferably, the internally threaded clip is press fit about the threaded post 32, such that it requires a predetermined upward force to remove it. It will be readily apparent to those of ordinary skill in the art that other retainer configurations may also be utilized, from a simple set screw to more complicated mechanisms.

Figure 5:
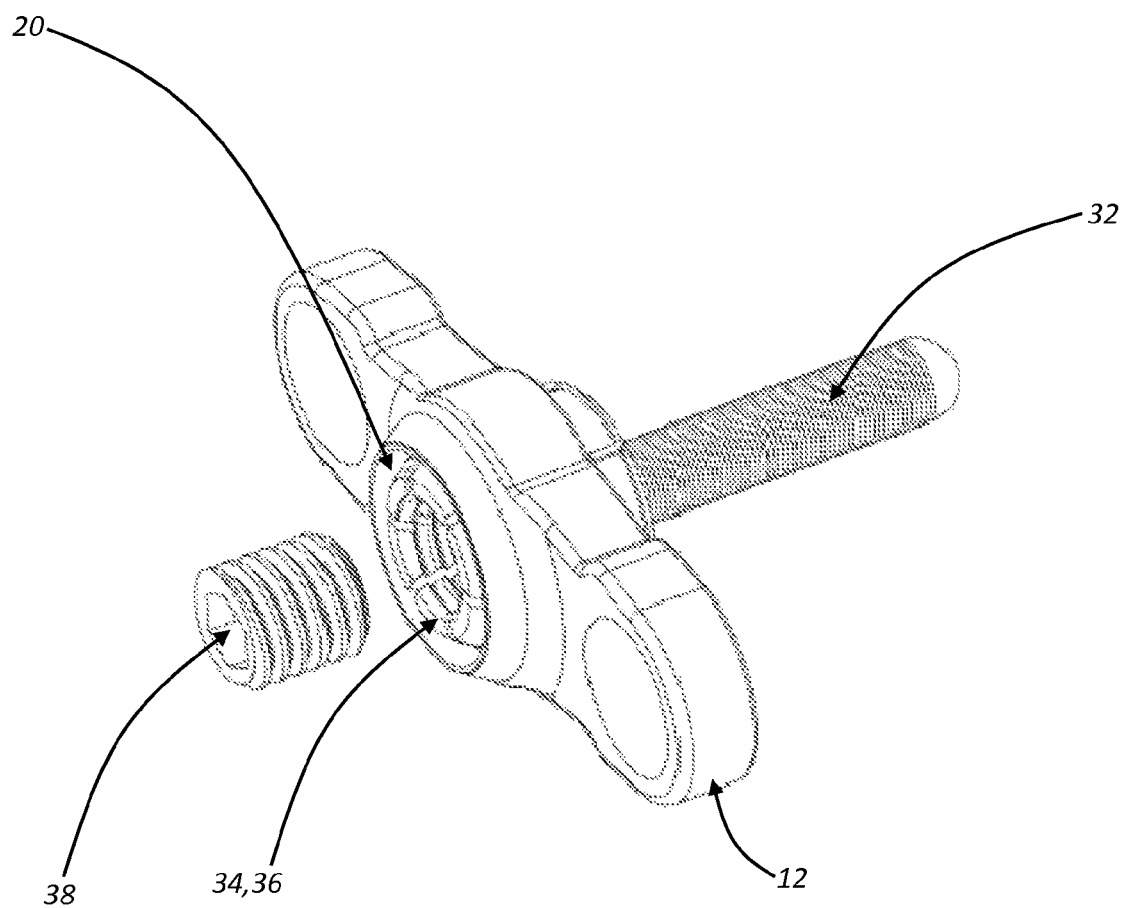
FIG. 5 is an exploded partial perspective view of one exemplary embodiment of the interspinous fusion device of the present invention, in a disassembled configuration.

FIG. 5 again illustrates that the substantially spherical head 34 may include appropriate petal structures 36 that allow the threaded post 32 to be seated in place, while allowing the threaded post 32 to pivot to some degree within the spherical bore 20. The threaded post 32 also includes a set screw 38 that is selectively disposed within the substantially spherical head 34 and tightened, thereby expanding the petal structures 36 against the spherical bore 20 and preventing the first plate 12 from pivoting relative to the second plate in the second locked configuration. Again, it will be readily apparent to those of ordinary skill in the art that other pivoting configurations may also be utilized.

Thus, again, in various exemplary embodiments, the present invention provides a novel interspinous fusion device that is configured to (optionally) distract and hold adjacent spinous processes of the spine of a patient in a fixed relationship to one another in the treatment of such conditions as lumbar spinal stenosis and degenerative disc disease, by way of non-limiting example only. Advantageously, the interspinous fusion device of the present invention may be inserted using a conventional open procedure, typically requiring a relatively large incision and a general anesthetic, or using a minimally invasive procedure, typically requiring a relatively small incision and a local anesthetic.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims.

What is claimed is:

1. An interspinous fusion device for holding adjacent spinous processes of a spine of a patient in a fixed configuration, comprising:
a first plate defining a central bore and configured to engage one side of the adjacent spinous processes;
a second plate defining a central bore and configured to engage another side of the adjacent spinous processes opposite the one side of the adjacent spinous processes;
a spacer disposed between and coupling the first plate to the second plate at the central bore of each, wherein the spacer allows one or more of the first plate and the second plate to pivot relative to the other plate in a first unlocked configuration and prevents one or more of the first plate and the second plate from pivoting relative to the other plate in a second locked configuration; and
a retention member for securing the second plate to the spacer, such that the spacer cannot "back out" of the second plate, wherein the retention member comprises a clip defining an open end slot leading to a central hole, wherein the clip is disposed through a port defined by the second plate perpendicular to the associated central bore and about a portion of the spacer within the associated central bore wherein the open end slot has a maximum width that is smaller than the diameter of the central hole.

2. The interspinous fusion device of claim 1, wherein each of the first plate and the second plate comprises a pair of opposed wing members protruding from the associated central bore.

3. The interspinous fusion device of claim 2, wherein each of the pair of opposed wing members comprises a friction surface configured to engage the associated spinous process.

4. The interspinous fusion device of claim 3, wherein the friction surface is pivotably coupled to the associated wing member.

5. The interspinous fusion device of claim 1, wherein the spacer comprises a threaded post disposed between and coupling the first plate to the second plate.

6. The interspinous fusion device of claim 5, wherein the threaded post comprises a substantially spherical head that is configured to engage a substantially spherical bore of the first plate, thereby allowing the first plate to pivot relative to the second plate in the first unlocked configuration.

7. The interspinous fusion device of claim 6, wherein the threaded post comprises a set screw that is selectively disposed within the substantially spherical head, thereby preventing the first plate from pivoting relative to the second plate in the second locked configuration.

8. The interspinous fusion device of claim 5, wherein the threaded post comprises an externally threaded end that is configured to engage the central hole, wherein the central hole is internally threaded.

9. The interspinous fusion device of claim 1, wherein the spacer further comprises a distraction member coupled to the first plate that is configured to be selectively disposed between the adjacent spinous processes.

10. The interspinous fusion device of claim 9, wherein the distraction member is one or more of pivotably and rotatably coupled to the first plate.

11. An interspinous fusion method for holding adjacent spinous processes of a spine of a patient in a fixed configuration, comprising:
providing a first plate defining a central bore and configured to engage one side of the adjacent spinous processes;
providing a second plate defining a central bore and configured to engage another side of the adjacent spinous processes opposite the one side of the adjacent spinous processes;
providing a spacer disposed between and coupling the first plate to the second plate at the central bore of each, wherein the spacer allows one or more of the first plate and the second plate to pivot relative to the other plate in a first unlocked configuration and prevents one or more of the first plate and the second plate from pivoting relative to the other plate in a second locked configuration; and
providing a retention member for securing the second plate to the spacer, such that the spacer cannot "back out" of the second plate, wherein the retention member comprises a clip defining an open end slot leading to a central hole, wherein the clip is disposed through a port defined by the second plate perpendicular to the associated central bore and about a portion of the spacer within the associated central bore wherein the open end slot has a maximum width that is smaller than the diameter of the central hole.

12. The interspinous fusion method of claim 11, wherein each of the first plate and the second plate comprises a pair of opposed wing members protruding from the associated central bore.

13. The interspinous fusion method of claim 12, wherein each of the pair of opposed wing members comprises a friction surface configured to engage the associated spinous process.

14. The interspinous fusion method of claim 13, wherein the friction surface is pivotably coupled to the associated wing member.

15. The interspinous fusion method of claim 11, wherein the spacer comprises a threaded post disposed between and coupling the first plate to the second plate.

16. The interspinous fusion method of claim 15, wherein the threaded post comprises a substantially spherical head that is configured to engage a substantially spherical bore of the first plate, thereby allowing the first plate to pivot relative to the second plate in the first unlocked configuration.

17. The interspinous fusion method of claim 16, wherein the threaded post comprises a set screw that is selectively disposed within the substantially spherical head, thereby preventing the first plate from pivoting relative to the second plate in the second locked configuration.

18. The interspinous fusion method of claim 15, wherein the threaded post comprises an externally threaded end that is configured to engage the central hole, wherein the central hole is internally threaded.

19. The interspinous fusion method of claim 11, wherein the spacer further comprises a distraction member coupled to the first plate that is configured to be selectively disposed between the adjacent spinous processes.

20. The interspinous fusion method of claim 19, wherein the distraction member is one or more of pivotably and rotatably coupled to the first plate.

21. An interspinous fusion device for holding adjacent spinous processes of a spine of a patient in a fixed configuration, comprising:
a first plate defining a central bore and configured to engage one side of the adjacent spinous processes;
a second plate defining a central bore and configured to engage another side of the adjacent spinous processes opposite the one side of the adjacent spinous processes;

a spacer disposed between and coupling the first plate to the second plate at the central bore of each, wherein the spacer allows one or more of the first plate and the second plate to pivot relative to the other plate in a first unlocked configuration and prevents one or more of the first plate and the second plate from pivoting relative to the other plate in a second locked configuration; and a retention member for securing the second plate to the spacer, such that the spacer cannot "back out" of the second plate, wherein the retention member comprises an internally threaded clip defining an open end that is disposed through a port defined by the second plate perpendicular to the associated central bore and press fit about a portion of the spacer within the associated central bore.

* * * * *